United States Patent [19]
Herbert

[11] Patent Number: 5,906,210
[45] Date of Patent: May 25, 1999

[54] SURGICAL PROCEDURE FOR RESTORATION OF STABILITY AND PAINFREE ROTATION OF THE DISTAL RADIO-ULNAR JOINT

[75] Inventor: Timothy Herbert, Sydney NSW 2107, Australia

[73] Assignee: Stuckenbrock Medizintechnik GmbH, Tuttlingen, Germany

[21] Appl. No.: 08/873,700

[22] Filed: Jun. 12, 1997

[51] Int. Cl.[6] .......................... A61B 19/00; A61B 17/00; A61F 2/42

[52] U.S. Cl. .............. 128/898; 623/21; 623/13; 606/79; 606/86

[58] Field of Search .................. 623/11, 13, 21; 128/897, 898; 606/79, 80, 86, 90

[56] References Cited

U.S. PATENT DOCUMENTS

| | | | |
|---|---|---|---|
| 4,164,793 | 8/1979 | Swanson | 623/21 |
| 4,198,712 | 4/1980 | Swanson | 623/21 |
| 5,458,646 | 10/1995 | Giachino et al. | 623/21 |
| 5,702,470 | 12/1997 | Menon et al. | 623/21 |
| 5,779,709 | 7/1998 | Harris, Jr. et al. | 606/87 |

*Primary Examiner*—Mickey Yu
*Assistant Examiner*—Dinh X. Nguyen
*Attorney, Agent, or Firm*—Jacobson, Price, Holman & Stern, PLLC

[57] ABSTRACT

A method for restoration of stability and painfree rotation of the distal radio-ulna joint is based on raising the capsulo-retinacular flap by dissection off the dorsal part of the triangular fibro-cartilage complex distally and off the neck of the ulna proximally. After resection of the ulna head and reaming the distal end of the ulna to an appropriate depth and inserting the prosthesis into a suitable position the dorsal aspect of the triangular fibro-cartilage complex is reattached to the underside of the flap. Finally, the flap is reattached to the sigmoid notch of the radius and the wound is closed. By this way, painfree forearm rotation is restored and at the same time any length discrepancy is corrected.

17 Claims, 5 Drawing Sheets

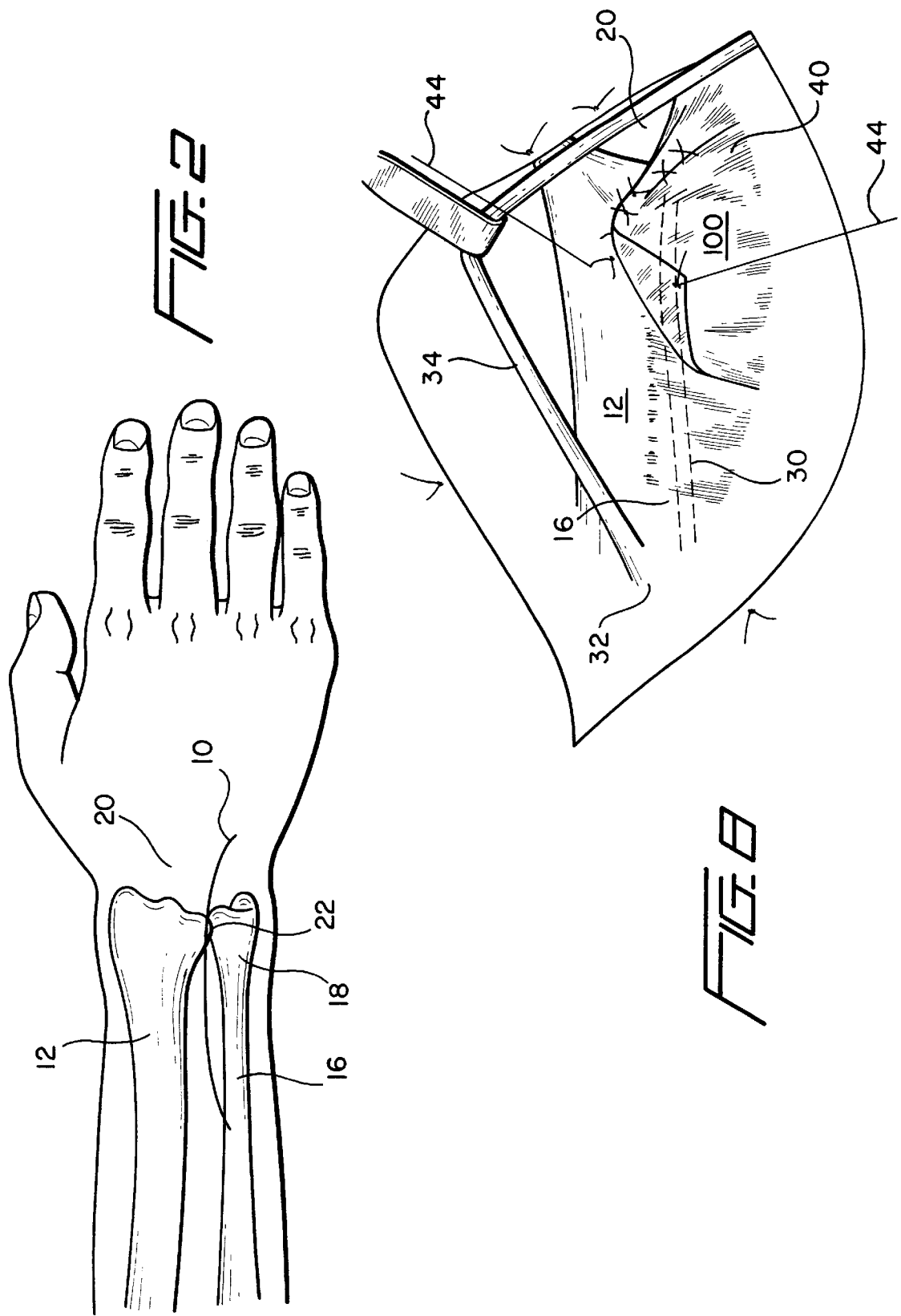

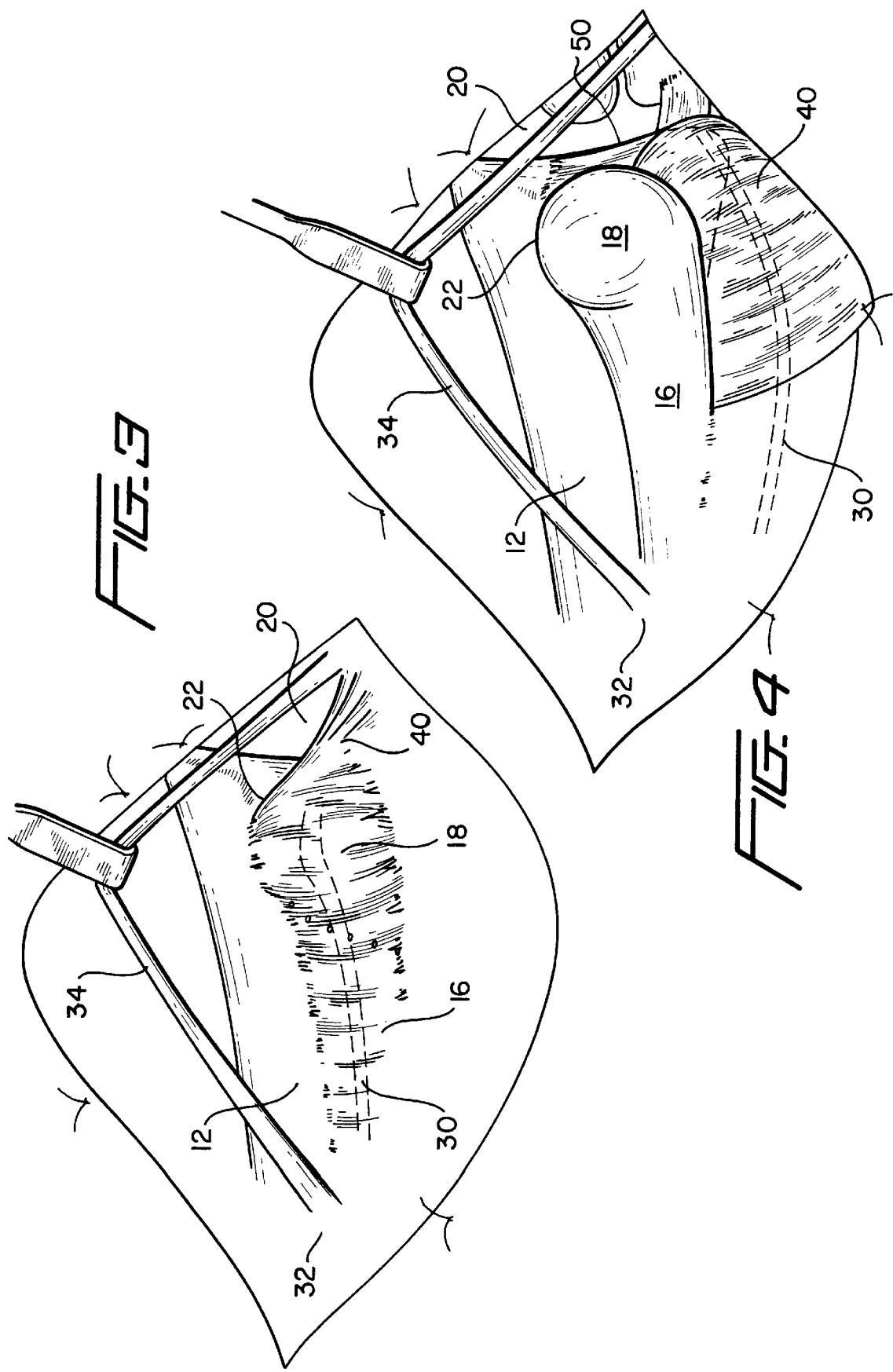

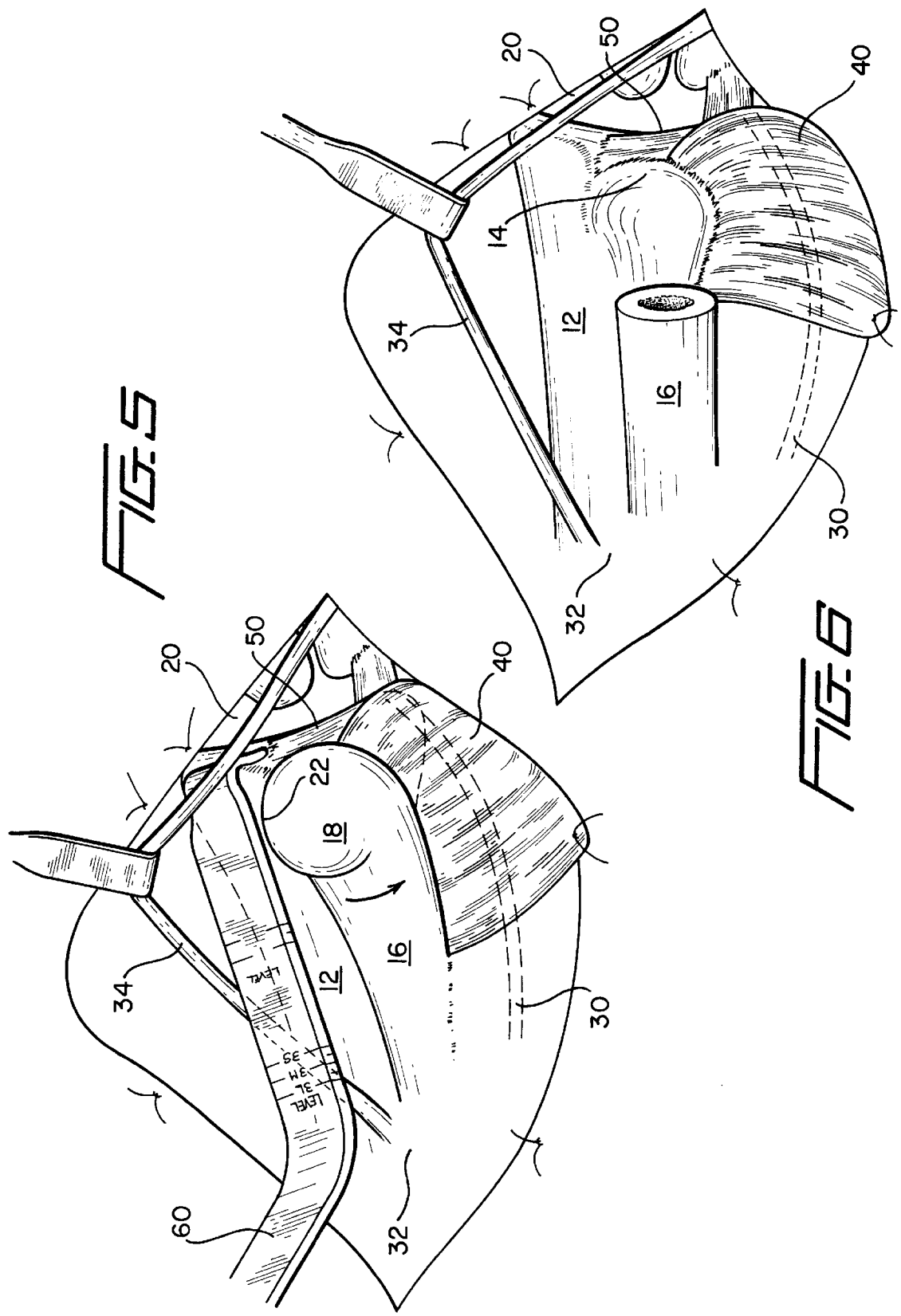

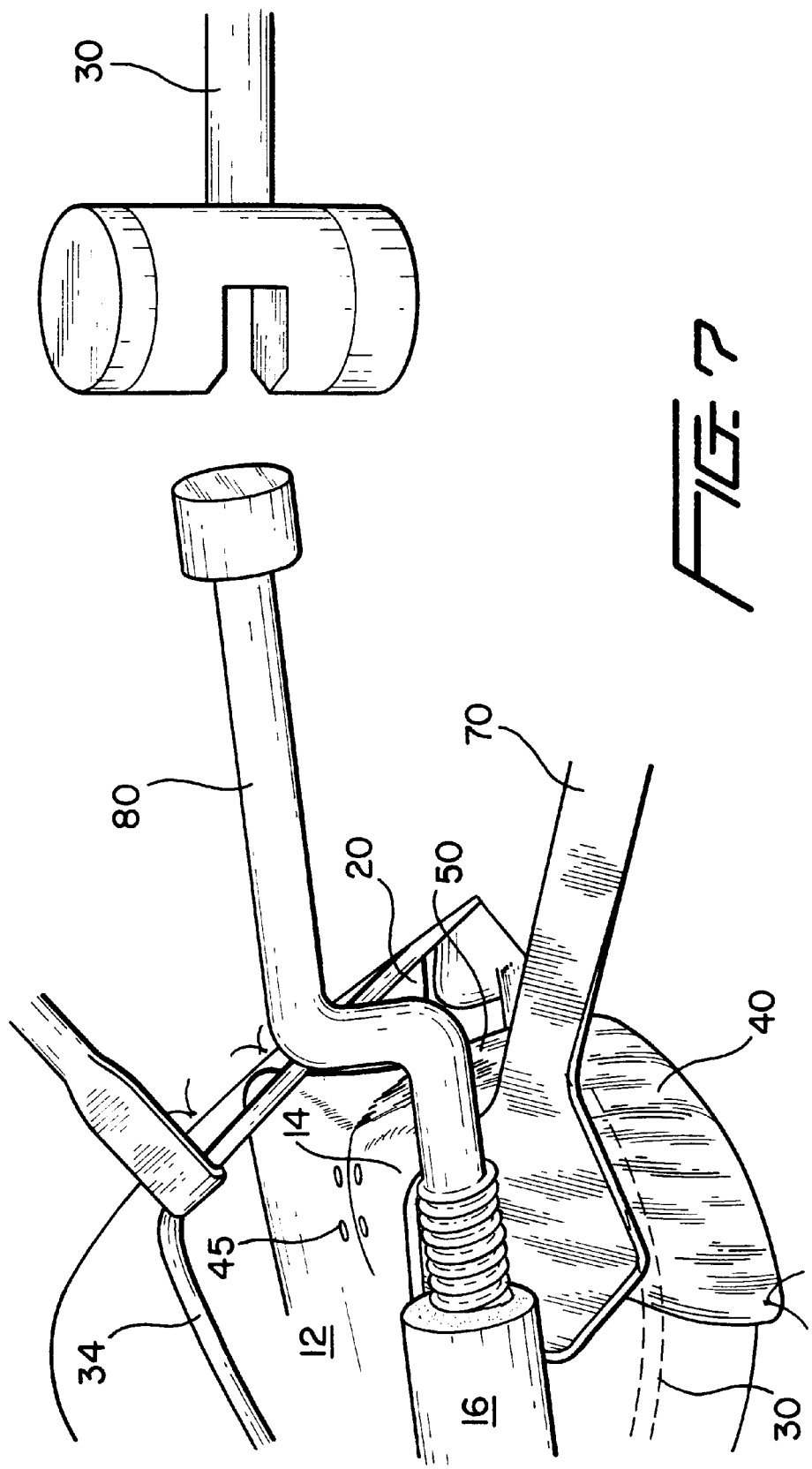

SURGICAL PROCEDURE FOR RESTORATION OF STABILITY AND PAINFREE ROTATION OF THE DISTAL RADIO-ULNAR JOINT

BACKGROUND OF THE INVENTION

1. Field of the Invention

The present invention relates generally to the operative treatment of the distal radio-ulnar joint and more particularly to the restoration of painfree rotation of the forearm and stability of the ulna and wrist by means of a soft tissue repair combined with a reconstruction of the triangular fibro-cartilage complex.

2. Relevant Background

The distal radio-ulnar joint consists of a shallow "ball and socket" articulation between the head of the ulna and the sigmoid fossa of the radius (FIG. 1a). This articulation allows for 180° of forearm rotation which is essential for normal function of the hand. The triangular fibro-cartilage complex acts as a cushion between the head of the ulna and the proximal row of the carpus. By means of its strong soft tissue attachments to the apex of the ulnar head and the capsule of the distal radio-ulnar joint, it is also the major stabiliser of the distal radio-ulnar joint. Similarly, its distal expansions merge with the wrist capsule to stabilise the ulnar side of the carpus on the wrist. It allows for a free range of flexion, extension, ulnar deviation at the ulno-carpal joint.

Disorders of the distal radio-ulnar joint are common and usually associated with pain, weakness, instability and loss of forearm rotation. Any loss of congruity between the sigmoid fossa of the radius and the ulnar head will result in painful loss of forearm rotation. Causes include congenital abnormalities such as Madelung's deformity, radial fractures, inflammatory arthritis and tears of the triangular fibro-cartilage complex. Tears of the triangular fibro-cartilage complex are extremely common, particularly in patients with ulnar plus variance. Tears may be due to acute or chronic trauma, and leads to pain and loss of motion in the ulnar side of the wrist. The loss of integrity of the triangular fibro-cartilage complex results in instability of both the distal radio-ulnar joint and the ulno-carpal joint which is likely to result, in time, in a fixed deformity leading to a secondary osteoarthritis. If normal alignement between the distal radius and ulna is lost an "ulnar plus" deformity will increase to the extent that the ulna starts to impact on the lunate and/or triquetrum. This impaction may result in triquetro-lunate instability and ulno-carpal osteoarthritis.

The most common cause of these problems is fracture of the distal radius. This may be associated with avulsion fracture of the ulnar styloid process, leading to fractional instability of the triangular fibro-cartilage complex. More commonly radial malunion results in a secondary ulnar plus deformity. Occasionally direct damage to the sigmoid fossa may lead to the development of secondary osteoarthritis.

Furthermore, trauma may result in acute dislocation of the distal radio-ulnar joint itself, often in association with radial head fracture and tear of the interosseous membrane.

Other conditions affecting the distal radio-ulnar joint and triangular fibro-cartilage complex include growth disorders (Madelung's deformity), primary osteoarthritis, metabolic disorders (e.g. gout), rheumatoid arthritis.

Finally, many patients suffer from painful instability following previous surgical procedures on the distal radio-ulnar joint.

Several prior art operative procedures exist regarding the removement of disorders of the distal radio-ulnar joint.

Darrach's procedure comprises the excision of the ulnar head and thus destabilises the triangular fibro-cartilage complex leading to ulno-carpal and radio-ulnar instability often resulting in painful radio ulnar impingement (FIG. 1b).

Bowers procedure attempts to overcome the above-mentioned problems by preserving the attachment of the triangular fibro-cartilage complex to the ulnar styloid process, thus retaining some stability (FIG. 1c). However, soft tissue interposition between the sigmoid fossa and the resected surface of the ulna is seldom strong enough to prevent some degree of ulno-carpal and radio-ulnar instability, due to loss of the normal alignement between the radius and the ulna. Furthermore, in cases of ulnar plus variance, ulno-carpal impaction will occur unless the ulna is shortened at the same time.

Another surgical treatment is the Sauve-Kapandji procedure (FIG. 1d) which relieves any ulno-carpal impaction whilst maintaining function of the triangular fibro-cartilage complex if performed correctly. However, rotation is only restored at the expense of an unstable ulnar pseudoarthrosis which commonly results in painful radio-ulnar impingement. Furthermore, exact positioning of the radio-ulnar fusion is difficult which may lead to ulno-carpal impaction and triangular fibro-cartilage complex problems.

To prevent radio-ulnar instability following ulnar head resection silastic ulnar head replacement was designed (Swanson, FIG. 1e). With modifications it may also allow for reconstruction of the triangular fibro-cartilage complex and restoration of ulno-carpal instability. However, the silastic prosthesis is subject to excessive wear which may be complicated by the development of silicone synovitis. As a result many of these prostheses have had to be removed resulting in painful ulno-carpal instability.

Although any of the above procedures may produce reasonable results if correctly carried out and in appropriate patients, there are, however, many patients who are discontented with the results of surgery and who are seeking a suitable revision procedure to restore stability and painfree rotation at the distal radio-ulnar joint. None of the above-mentioned prior art operative procedures comprises a surgical treatment which can be guaranteed to restore painfree rotation and at the same time correct any underlying instability of length discrepancy.

It is therefore the object of the present invention to provide a new operative procedure for restoration of the distal radio-ulnar joint which, combined with a careful reconstruction of the triangular fibro-cartilage complex and the use of a ulnar based capsulo-retinacular flap, results in stability and painfree rotation.

SUMMARY OF THE INVENTION

The present invention provides a surgical procedure to restore a painfree rotation and stability of the ulna and wrist by means of a soft tissue repair combined with a reconstruction of the triangular fibro-cartilage complex (FIG. 1f).

After dorsal incision centered over the distal radio-ulnar joint the capsulo-retinacular flap is raised by incising through the capsule and dissection off the dorsal part of the triangular fibro-cartilage complex distally and off the neck of the ulna proximally.

After raising stay sutures may be used to retract the flap in a suitable position while exposing the distal radio-ulnar joint and the ulno-carpal joint. The subsequent resection of the ulna head may be followed by careful inspection of the triangular fibro-cartilage complex which may be, if necessary, repaired using fine non-absorbable sutures. After reaming the distal end of the ulna by use of a sharp awl and a reamer, trial reduction and assessment of a trial stem and head may be performed by advancing the flap radially over the ulnar head. If a suitable size of prosthesis stem and head are determined the definitive prosthesis is inserted and the flap is closed. The dorsal aspect of the triangular fibro-cartilage complex is reattached to the underside of the flap. Finally, the flap is carefully advanced until it is tight enough to provide complete stability and reattached under appropriate tension to the sigmoid notch of the radius.

BRIEF DESCRIPTION OF THE DRAWINGS

FIG. 2 illustrates the incision line on the dorsal side of the hand centered over the distal ulnar-radio joint.

FIG. 3 represents the capsulo-retinacular flap which is marked for dissection off the dorsal part of the triangular fibro-cartilage complex distally and off the neck of the ulna proximally.

FIG. 4 shows the distal ulnar-radio joint after raising the capsulo-retinacular flap and fixation thereof by means of stay sutures.

FIG. 5 illustrates the use of a resection guide template to ensure optimum positioning of the head of the prosthesis.

FIG. 6 represents the ulnar stump after ulnar head resection.

FIG. 7 shows a reamer during insertion into the ulnar stump by means of a hammer while holding down the soft tissue placing a retractor under the distal end of the ulna.

FIG. 8 illustrates the capsulo-retinacular flap after reattachment of the triangular fibro-cartilage complex and advancing over the head of the prosthesis.

DETAILED DESCRIPTION OF A PREFERRED EMBODIMENT

Figure 1D:
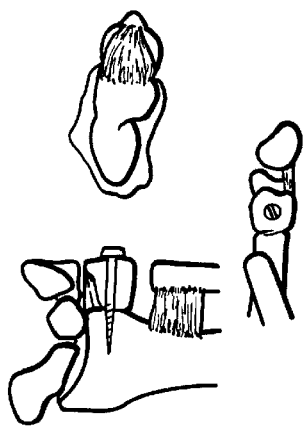
FIG. 1d; Swanson's procedure.
Figure 1E:
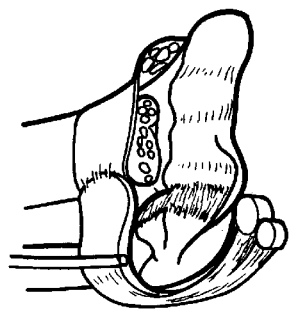
FIG. 1e)
Figure 1F:
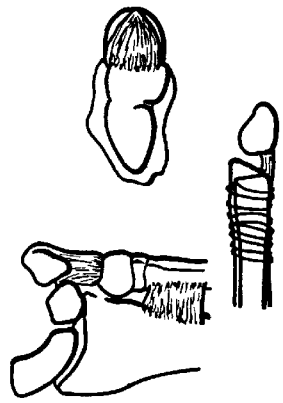
FIG. 1 represents the rotation of radius on the ulna (FIG. 1a) and prior art surgery procedures (FIG. 1b–1e) as well as stabilisation of the prosthesis by an ulnar flap (FIG. 1f) (Darrach's procedure.
FIG. 1b; Bowers procedure.
FIG. 1c; Sauve-Kapandji procedure.
Figure 1A:
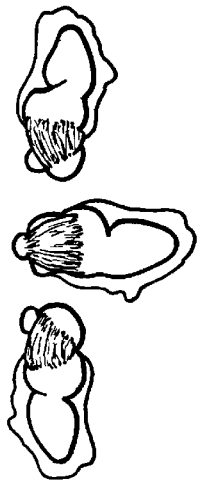
Figure 1B:
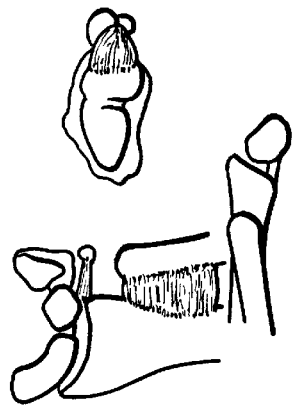
Figure 1C:
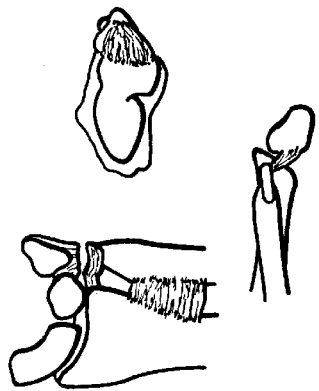

Before surgical operation careful clinical examination is required in order to assess accutely the extent of instability of the ulna and/or the carpus. Similarly it is important to recognize any fixed deformity or dislocation, as this will need to be corrected at the time of surgery.

It dorsal subluxation of the ulna is due to an underlying radial deformity, this must be corrected by means of an appropriate radial osteotomy. Standard 90/90 degree X-rays of both forearms and wrists have to be obtained preoperatively. The appropriate X-ray template should then be used to assess optimum resection level and a likely size of head and stem required. Comparison with the opposite normal wrist is the most helpful way to determine the appropriate resection level.

The operation is carried out with the arm extended on an operating side table in full pronation and under tourniquet control. X-ray control, using a fluorescan is highly desireable.

As a first step of the claimed operative procedure a 6–8 cm straight dorsal incision 10 is made, centered over the distal radio-ulna joint 20 (FIG. 2). In the case of a revision procedure, the incision 10 should take account of previous scars and also extend proximally to allow adequate exposure of the shaft of the ulna 16.

The dorsal sensory branch of the ulna nerve is found and retracted together with the volar skin flap. Awareness of the possibility of the transverse branch of this nerve which passes towards the radial side of the wrist at a level of the ulno-carpal joint is necessary.

The fifth extensor compartment 32 is opened longitudinally and the extensor digiti minimi tendon 34 is mobilized and retracted radially.

Subsequently a capsulo-retinacular flap 40 is marked out as shown in FIG. 3. The base of the flap 40 is centered on the pisiform bone with its apex at the mid-point 22 of the distal radio-ulnar joint 20. Raising of the flap 40 is started by incising through the capsule where it attaches to the rim of the sigmoid fossa 14. The flap 40 is then carefully raised by sharp dissection off the dorsal part of the triangular fibro-cartilage complex 50 distally and off the neck of the ulna 16 proximally.

Stay sutures are used to retract the flap 40, allowing exposure of both the distal radio-ulnar joint 20 and ulno-carpal joints (FIG. 4). The sixth extensor compartment 30 should not be opened as this forms an integral part of the base of flap 40.

If the floor of the sixth compartment 30 is deficient, due to degenerative process or previous surgery, this should be repared using fine interrupted mattress sutures so that the extensor carpi ulnaris tendon is no longer visible but is contained within the base of the flap 40.

For revision procedures the soft tissues between the ulna 16 proximally and the near edge of the flap 40 distally are incised longitudinally and reflected as one layer to expose the ulnar stump.

After raising the capsulo-retinacular flap 40 the neck of the ulna 16 is exposed using Hohmann retractors. The resection level is then marked using a resection guide template 60 (FIG. 5). This ensures that the head of the prosthesis will lay in the optimum position, which is 2 mm proximal to the triangular fibro-cartilage complex 50. The tip of the resection guide 60 is carefully inserted over the distal end of the radius 12 at its extreme ulnar border. Dependent of the degree of ulnar shortening different levels of the ulna head resection are adequate.

Level 1 resection is used for the standard prosthesis and is the preferred resection level. Level 2 may be used when there is insufficient bone stock to allow for seating the prosthesis more distally. The standard+stem should be used at this level to ensure optimum length of the prosthesis (at 2 mm ulnar minus). Similarly, because of the length discrepancy between the three head sizes (+2 mm/–2 mm) of the head of the prosthesis level 2 may be selected when using a large had, again to ensure optimum length of the prosthesis. Level 3 is used only with the revision stem, in case of extreme ulnar shortening, which e.g. is present after previous surgery such as Darrach's procedure.

Resection should be carried out at the appropriate level depending on the size of head selected. It was found that the full range could be covered by having 3 stem diameters and 3 head sizes of the prosthesis. Further, it was recognized that there would be a need for a revision stem with a built up neck to compensate for excessive shortening associated with previous surgical procedures.

The stem should be designed to have a "contact fit" within the medullary canal of the ulna 16, with a porous surface for bone ingrowth so that cement fixation would not be required. Interchangeable stem and head sizes demanded for the use of a "morse lock" between the two components. The head is designed to conform with the diameter of the sigmoid fossa 14, restoring the normal alignment between the radius 12 and the ulna 16, and providing a support underlying the soft tissue flap repair.

The distal end of the head is concave in order to avoid excessive pressure on the underside of the triangular fibro-cartilage complex 50. Ceramic is chosen as the most biocompatible material with the best wear characteristics for use as a hemiarthroplasty.

As the flap repair has been shown to provide adequate tension in the triangular fibro-cartilage complex 50 and to give excellent stability both in the distal radio-ulnar 20 and ulno-carpal joints, no soft tissue attachment points on the prosthesis are provided.

In a next step of the procedure the ulnar head 18 is grasped with the holding forceps and is rotated externally and distally (see arrow in FIG. 5) so that the soft tissue attachments can be carefully peeled away using a combination of blunt and sharp dissection. In this way the attachment of the apex of the triangular fibro-cartilage complex 50 to the underside of the flap 40 will be preserved. If there is an ununited ulnar styloid fragment, this may need to be removed separately and any resulting deficiency carefully repaired.

After resection of the ulna head 18 at the appropriate level, the triangular fibro-cartilage is carefully inspected and palpated both on its proximal and distal surfaces (FIG. 6). Any tears of deficiencies are repaired using fine 4/0 non-absorbable sutures. Where necessary, local soft tissue flaps may be used to reinforce the repair of the triangular fibro-cartilage. Furthermore, the triquetro-lunate joint is checked and stabilized as necessary. Finally, the sigmoid fossa 14 is examined and cleared of any scare tissue or osteophytes which may interfere with seating of the head of the prosthesis 100. In selected cases the sigmoid fossa 14 may be despend with a power reamer in order to enhance stability.

After examination of triquetro-lunate joint and sigmoid fossa 14 the appropriate sided soft tissue retractor 70 is placed under the distal end of the ulna 16 and the medullary cavity of the ulna 16 is opened by a sharp awl (FIG. 7). The standard small reamer is inserted by means of a hammer 90 into its maximum depth, at which stage it should be a tight fit. If no tight fit is achieved it is to be progressed to a medium or large reamer 80 as appropriate.

The slot of the hammer 90 is used to remove the reamer 80, which should always have been inserted to its full depth.

In the case of a revision procedure, only special revision reamers in similar fashion are to be used.

Furthermore, at this stage at least two small drill holes 15 should be made in the dorsal rim of the sigmoid notch, to facilitate insertion of perosseous sutures doing later flap repair.

Prior to insertion of the definitive prosthesis 100 an appropriate trial stem and head may be inserted into the ulnar stump. The fit of the stem and the position of the head (approximately 2 mm below the triangular fibro-cartilage complex 50) should be checked fluorescopically with the wrist in full pronation.

In order to check whether the flap 40 can be reattached to the radius 12 thus providing adequate stability the flap 40 is advanced radially over the ulnar head. If the flap 40 is too tight, the small head should be tried. If this is selected, the standard stem should be changed to a standard+stem in order to ensure optimum length of the prosthesis. On the other hand, if the flap is too loose, the large head may be selected. In this case, the ulna 16 must be shortened back to level 2 in order to ensure optimum length of the prosthesis (2 mm ulnar minus).

After assessment of the range of forearm rotation the trial prosthesis is removed, using the explanation chissels where necessary and the wound and medullary canal are irrigated.

After selection of suitable sizes the definitive stem and head are inserted. The stem is carefully hammered into position using the conical impactor. The conical end of the stem should be clean and dry before the ceramic head is impacted.

If for any reason it is necessary to remove the prosthesis 100, this can be done using the stem extractor. At this stage, intra-operative X-rays are used to confirm that the prosthesis 100 is in optimum position.

It is important not to use excessive force during insertion of the definitive prosthesis 100. If the stem appears to "lock" during insertion, it should be removed and further reaming carried out.

After inserting the definitive prosthesis 100 the dorsal aspect of the triangular fibro-cartilage complex 50 is reattached to the underside of the flap 40 using one or two fine non-absorbable mattress sutures 44 (FIG. 8). The flap 40 is then carefully advanced until it is tight enough to provide complete stability whilst still allowing full range of rotation. The flap 40 should be reattached under the appropriate tension to the dorsal rim of the sigmoid notch, using a perosseous suture technique (size "0" non-absorbable suture material is recommended). The remainder of the flap 40 is sutured using an overlap (2 layers) repair where appropriate. The extensor digiti minimi tendon 34 should be left free and no attempt should be made to reconstruct the fifth extensor compartment 32.

The proxial extension of the flap 40 along the ulna neck is sutured as is the distal extension overlying the ulno-carpal joint 20.

It is appropriate at this stage to make a final assessment in order to check that there is a full range of rotation with non abnormal crepitus or instability in either the radio-ulnar 20 or ulno-carpal joints.

After insertion of suction drains the wound is closed in an appropriate fashion and a firm wool and creep bandage is applied. A six-inch plaster slab is then moulded around the ulnar side of the wrist in order to protect the soft tissue repair.

While dressings are normally left intact until the sutures are removed at 12–14 days, however, where necessary, the dressings may be reduced and the appropriate splints and hand therapy can be commenced. Alternatively, if instability is more likely to be a problem, a "sugur tong" type splint is fitted as soon as possible in order to protect the repair and prevent forearm rotation. Where appropriate an elastic ulnar carpal support may be used as protection particularly for heave workers.

What is claimed is:

1. A surgical procedure for restoration of stability and painfree rotation of the distal radio-ulnar joint comprising the steps of:

dorsal incision centered over the distal radio-ulnar joint;

raising the capsulo-retinacular flap by incising through the capsule and dissection off the dorsal part of the triangular fibro-cartilage complex distally and off the neck of the ulna proximally;

resection of the ulna head;

reaming the distal end of the ulna to an appropriate depth and inserting the prosthesis into a suitable position;

reattachment of the dorsal aspect of the triangular fibro-cartilage complex to the underside of the flap and reattachment of the flap to the sigmoid notch of the radius and closing the wound.

2. A method according to claim 1, further comprising retraction of the dorsal sensory branch of the ulna nerve together with the volar skin flap.

3. A method according to claim 1, further comprising a step of longitudinally opening the fifth extensor compartment and mobilization and radially retraction of the extensor digiti minimi tendon.

4. A method according to claim 1, wherein the capsulo-retinacular flap is marked and the base of the flap is centered on the pisiform bone with its apex at the mid-point of the distal radio-ulnar joint.

5. A method according to claim 1, whereby incision of the capsule is performed where it attaches to the rim of the sigmoid fossa.

6. A method according to claim 1, whereby the sixth extensor compartment is not opened and forms and integral part of the base of the capsulo-retinacular flap.

7. A method according to claim 1, wherein the resection level is marked using a resection guide template, whereby the tip of the resection guide is carefully inserted over the distal end of the radius at its exteme ulnar border.

8. A method according to claim 1, further comprising the steps of grasping and externally and distally rotating the ulna head for peeling away soft tissue attachment using a combination of blunt and sharp dissection.

9. A method according to claim 1, further comprising the steps of inspection, palpation and eventually preparation of the triangular fibro-cartilage.

10. A method according to claim 1, whereby after resection of ulna head the sigmoid fossa is examined and cleared of any scar tissue or osteophytis or despend by means of a power reamer to enhance stability.

11. A method according to claim 1, further comprising the steps of opening the medullary cavity of the ulna by means of a sharp awl and hammering a reamer into its maximum depth, in which stage should be a tight fit.

12. A method according to claim 1, wherein at least two small drill holes are made in the dorsal rim of sigmoid notch.

13. A method for restoration of stability and painfree rotation of the distal radio-ulnar joint comprising the steps of:

dorsal incision centered over the distal radio-ulnar joint;

raising the capsulo-retinacular flap by incising through the capsule and dissection off the dorsal part of the triangular fibro-cartilage complex distally and off the neck of the ulna proximally;

resection of the ulna head;

reaming the distal end of the ulna to an appropriate depth and insertion and assessment of a trail prosthesis;

removal of the trial prosthesis and inserting the definitive prosthesis into a suitable position;

reattachment of the dorsal aspect of the triangular fibro-cartilage complex to the underside of the flap and reattachment of the flap to the sigmoid notch of the radius and closing the wound.

14. A method according to claim 13, whereby the trial prosthesis is located so that the head of prosthesis lies at an appropriate level below the triangular fibro-cartilage complex.

15. A method according to claim 1, further comprising the steps of advancing the capsulo-retinacular flap over the ulna head and change of trial or definitive prosthesis stem or head until adequate tension, length and stability are achieved.

16. A method according to claim 1 wherein the flap is reattached under appropriate tension to the dorsal rim of the sigmoid notch using a perosseous technique.

17. A method according to claim 1, further comprising the suture of the proximal extension of the flap along the ulna neck and the distal extension overlying the ulno-carpal joint.

* * * * *